(12) United States Patent
Durand et al.

(10) Patent No.: US 9,989,526 B2
(45) Date of Patent: Jun. 5, 2018

(54) METHOD AND DEVICE FOR BIOASSAYS

(71) Applicant: ABIONIC SA, Lausanne (CH)

(72) Inventors: Nicolas Durand, Vonnaz (CH); Iwan Märki, Yverdon-les-Bains (CH); Annick Mayor, Morges (CH); Stéphane Broillet, Ferlens (CH)

(73) Assignee: ABIONIC SA, Lausanne (CH)

(*) Notice: Subject to any disclaimer, the term of this patent is extended or adjusted under 35 U.S.C. 154(b) by 341 days.

(21) Appl. No.: 14/905,069

(22) PCT Filed: Jul. 7, 2014

(86) PCT No.: PCT/EP2014/064482
§ 371 (c)(1),
(2) Date: Jan. 14, 2016

(87) PCT Pub. No.: WO2015/007559
PCT Pub. Date: Jan. 22, 2015

(65) Prior Publication Data
US 2016/0153980 A1    Jun. 2, 2016

(30) Foreign Application Priority Data
Jul. 17, 2013 (EP) .................. 13176794

(51) Int. Cl.
*G01N 33/543* (2006.01)
*G01N 21/64* (2006.01)
*B01L 3/00* (2006.01)

(52) U.S. Cl.
CPC .. G01N 33/54386 (2013.01); B01L 3/502707 (2013.01); G01N 21/6428 (2013.01); G01N 21/6452 (2013.01); G01N 33/54373 (2013.01); *B01L 2300/0636* (2013.01); *B01L 2300/0896* (2013.01); *B01L 2400/0406* (2013.01)

(58) Field of Classification Search
None
See application file for complete search history.

(56) References Cited

U.S. PATENT DOCUMENTS

| 6,534,011 B1* | 3/2003 | Karthe | G01N 21/6428 422/82.01 |
|---|---|---|---|
| 9,452,927 B2* | 9/2016 | Durand | B82Y 15/00 |
| 2013/0017967 A1* | 1/2013 | Durand | B82Y 15/00 506/9 |

FOREIGN PATENT DOCUMENTS

| WO | 2011064701 A1 | 6/2011 |
| WO | 2012120387 A1 | 9/2012 |

OTHER PUBLICATIONS

International Search Reported dated Sep. 26, 2014, 9 pages.
International Search Report to Corresponding International Application No. PCT/EP2014/064482, dated Sep. 26, 2014, 9 pages.

* cited by examiner

*Primary Examiner* — Chris L Chin
(74) *Attorney, Agent, or Firm* — Cooper Legal Group LLC

(57) ABSTRACT

A method and device for multiplexing and calibrating rapid quantification of biomolecules present in a nanofluidic biosensor composed by a nanoslit. A novel concept defining multiple different local structured areas containing biomarkers. Local structured areas can also be structured to decrease the biomarkers density in the nanoslit. Such enables the multiplexed quantification biomolecular interactions of interest in the same nanofluidic biosensor.

15 Claims, 5 Drawing Sheets

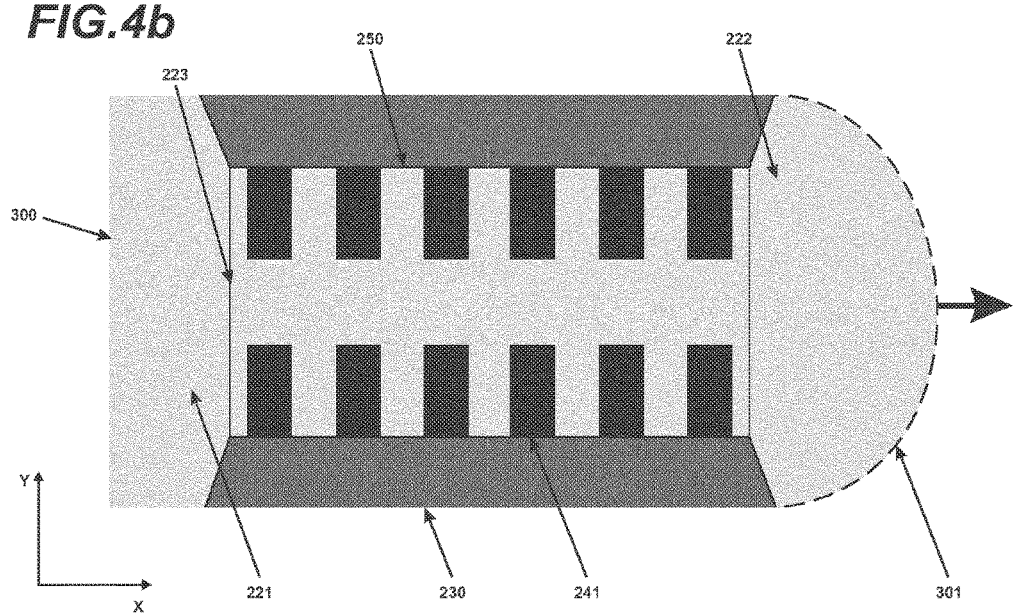
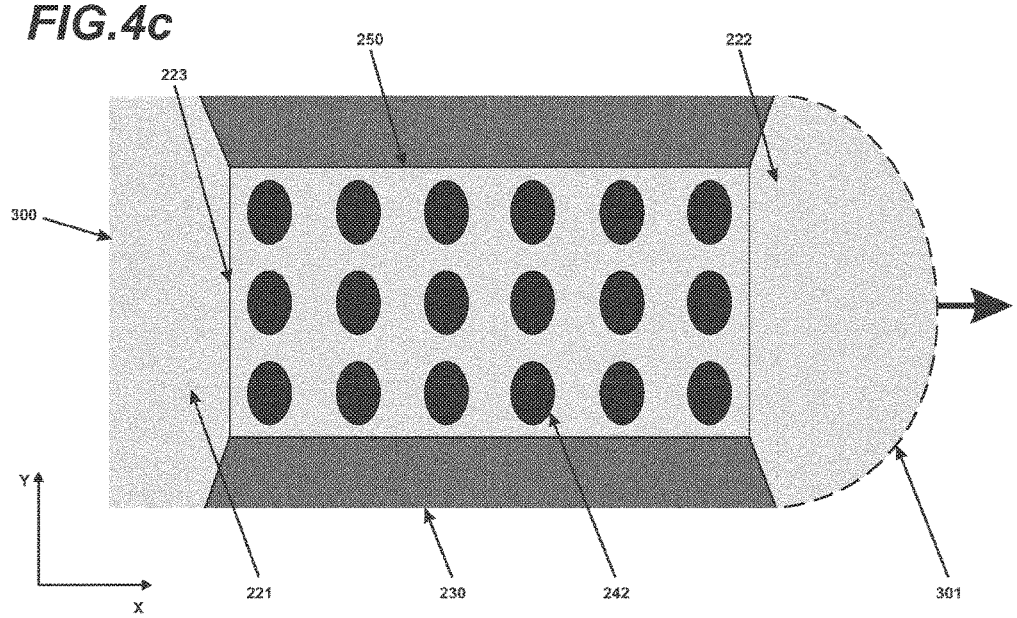

METHOD AND DEVICE FOR BIOASSAYS

FIELD OF INVENTION

The present invention relates to a method and to a device for the detection of various fluorescently labeled biomolecules in selectively functionalized nanofluidic biosensors, by means of an optical system. The present invention may for example be advantageously used for rapid quantification of biomedical and biological samples.

BACKGROUND OF THE INVENTION

Nanofluidic biosensors are fluidic systems with nanometer-sized confinements and/or lateral apertures, which are used to quantify the presence of biomolecules in a solution. Most nanofluidic biosensor developments are intended for bioengineering and biotechnology applications. In the scope of this invention, the biosensors are used for example to quantify the presence of biomolecules in a solution for in vitro diagnostic applications.

Swiss patent application CH 01824/09 discloses biosensors with lateral apertures for the detection of biomolecular interactions, PCT application PCT/IB2010/050867 discloses the use of such biosensors with simple optical systems and PCT application PCT/IB2011/050979 discloses a method for avoiding long waiting times to attain stable measurement conditions. However, in all configurations described in these documents, the number of type of biomarker was limited to one per nanofluidic biosensor.

Biomarkers, also called biological markers, are substances used as specific indicators for detecting the presence of specific biomolecules. It is a characteristic that is objectively measured and evaluated as an indicator of biological processes, pathogenic processes, or pharmacologic responses to a therapeutic intervention.

Methods for the detection of specific biomolecules can be divided in two categories: (a) the labeled techniques and (b) the label-free techniques.

Among the labeled techniques, the widely used ones are fluorescence, colorimetry, radioactivity, phosphorescence, bioluminescence and chemiluminescence. Functionalized magnetic beads can also be considered as labeling techniques. Advantages of labeled techniques in comparison to label-free methods are the sensitivity and the molecular recognition due to specific labeling.

Among the label-free techniques, the widely used ones are electrochemical biosensors, referring to amperometric, capacitive, conductometric or impedimetric sensors, which have the advantage of being rapid and inexpensive. They measure the change in electrical properties of electrode structures as biomolecules become entrapped or immobilized onto or near the electrode. These technologies however lack molecular specific contrast, sensitivity and reliability.

Enzyme linked immunosorbent assay (ELISA) is an important biochemical technique mainly used to detect the presence of soluble biomolecules in serum, and is thus widely used as a diagnostic tool in medicine and quality control checks in various industries. ELISA analysis are however expensive, require large amounts of solution and are time consuming.

The other relevant technologies for biomolecular diagnostics are Western and Northern blots, protein electrophoresis and polymerase chain reaction (PCR). However, these methods require highly concentrated analytes and do not allow high throughput samples testing.

Aims of the Present Invention

An object of the present invention is to provide inexpensive and fast self-calibrated or multiplexed nanofluidic biosensors, which do not require complex manipulations.

Still another object of the present invention is to geometrically confine the optical measurement volume down to the nanometer scale and to obtain a multiplexed high sensitive biosensor.

Still another object of the invention is to provide a biosensor able to provide a calibration curve, which can then be used to subtract the biosensor background and to provide quantitative measurements with the concentration value of specific measurements.

These and other objects of the present invention will become apparent with reference to the following description of preferred embodiments, illustrated by the figures.

SUMMARY OF THE INVENTION

According to embodiments of the present invention, several functionalized areas are differently patterned in order to vary the density of immobilized biomarkers in a nanofluidic biosensor, thereby allowing the extraction of a calibration curve that depends on the biosensor environment and on the solution filling the biosensor.

Furthermore, according to embodiments of the present invention, various biomarkers are immobilized on various functionalized areas in a same nanofluidic biosensor, thereby allowing quantifying multiple types of biomolecules in the same nanofluidic biosensor.

In the present text the term "patterned functionalized areas" has to be understood as surfaces that are structured in a way that the total surface where biomarkers are immobilized, is limited according to a determined pattern. The patterning can be realized by the geometry of one or more functionalized surfaces or by varying the concentration of the biomarkers within a specific area.

In the scope of this invention, nanofluidics is used because of its high surface-to-volume ratio, which means that the surfaces comprised in the detection volume maximize the probability of interaction between biomolecules and the biomarkers immobilized on said surfaces. Nanofluidics also strongly reduces the background signal of the solution due to the small portion of substrate that is within the detection volume.

The invention relates to a biosensor as defined in the claims.

It also relates to an assembly and a method using said biosensor.

BRIEF DESCRIPTION OF THE DRAWINGS

FIGS. 4a, 4b and 4c are a partial top view cross sections of biosensors according to different embodiments of the invention, where the nanofluidic biosensor comprises a nanoslit 223 with a lateral input aperture 221, a lateral output aperture 222, and sides 223. The solution 300 containing biomolecules enters the nanoslit 223 with a flow front 301. Several functionalized areas 240, 241, 242 and not functionalized areas 250 are present in the nanoslit 223. Functionalized areas 240, 241, 242 may have various shapes such as lines 240, small polygons 241 or rounded areas 242.

DETAILED DESCRIPTION OF THE INVENTION

As used herein, the term "system" is intended to be a generic term, which includes for example (but not limited to) a capsule, a surface, a disc or any environment that can immobilize nanofluidic biosensors.

As used herein, the term "biomolecules" is intended to be a generic term, which includes for example (but not limited to) proteins such as antibodies or cytokines, peptides, nucleic acids, lipid molecules, polysaccharides and virus.

As used herein, the term "nanoslit" is intended to be a generic term, which means well-defined microfabricated structure with one nanometer-sized dimension. The nanometer-sized dimension of the nanoslit is defined to be higher than 2 nm because of the size of the smallest biomolecules to be detected that have to enter into the slit and that are in the same order of magnitude. The present invention is limited to nanoslit with only one dimension lower than one micron, because of the range of the detection volume of the optical system that are typically in the same order of magnitude.

An object of the present invention, according to embodiments, is to allow the detection of several substances, in particular of several biomolecules in a single nanofluidic biosensor.

Figure 1:
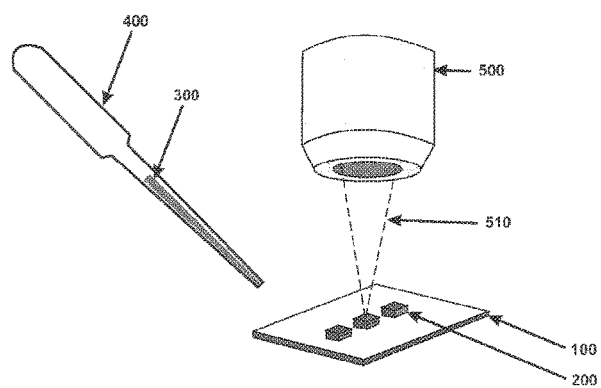
FIG. 1 is a perspective schematic view of a system 100 comprising nanofluidic biosensors 200 with lateral apertures. A solution 300 containing fluorescently-labeled biomolecules is deposited in the system 100 by a pipet system 400. An optical system 500 including a probing laser 510 is used for the measurement.

As illustrated in FIG. 1, according to embodiments of the invention, several nanofluidic biosensors 200 are immobilized in a system 100. A mixed solution 300 containing fluorescently-labeled biomolecules of interest is deposited inside the system 100 for example with a pipet system 400. An optical unit 500 is used to measure the biomolecular interactions inside the biosensors 200 by focusing the laser beam 510 inside the biosensors' nanoslit.

Figure 2:
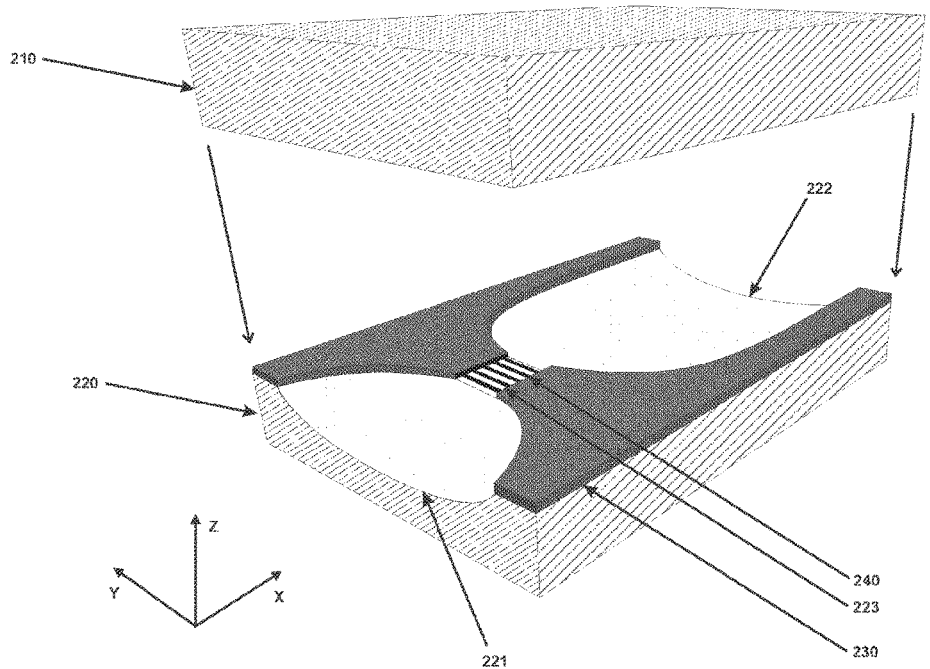
FIG. 2 is a perspective view of an embodiment of a nanofluidic biosensor 200 with a lateral input aperture 221 and a lateral output aperture 222. A nanoslit 223, which is a nanometer sized slit, is defined by the height of a structured material 230 sandwiched between a first substrate 210 and a second substrate 220. Several functionalized areas 240 are present in the nanoslit 223.

FIG. 2 illustrates the structure of a nanofluidic biosensor according to an embodiment of the invention. A layer 230 of a thickness ranging for example from 2 to 1,000 nm is deposited on a lower substrate 220 and structured using standard photolithography techniques in order to define the geometry of a nanoslit 223. An upper substrate 210 is added, or stacked, onto the lower substrate 220. At least one of the lower or upper substrates has to be compatible with the microscope objective in terms of transparency and optical aberrations. The nanofluidic biosensor also comprises an input lateral aperture 221 and an output lateral aperture 222. The nanoslit 223 is in fluidic communication with said lateral apertures 222, 223 and links the input lateral aperture 221 with the output lateral aperture 222. The nanoslit's height is determined by the spacing between the upper and the lower substrates 210, 220, i.e. by the thickness of layer 230. The layer 230 thus acts as a spacer to define the height of the nanoslit 223. Several areas 240 inside the nanoslit 223 are functionalized for the detection of biomolecules.

Figure 3:
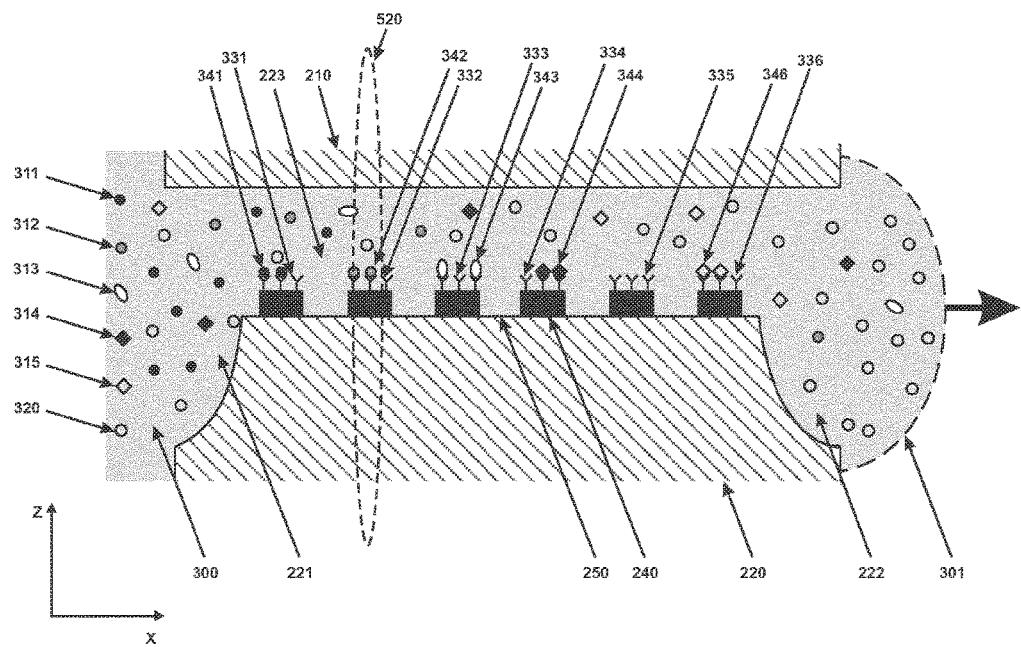
FIG. 3 is a schematic representation of a partial cross section of the nanofluidic biosensor of FIG. 2, comprising two substrates 210 and 220 and locally structured areas 240 that are each functionalized by different biomarkers 331, 332, 333, 334, 335, 336 and other areas 250 that prevent that functionalization. The solution 300 containing biomolecules 311, 312, 313, 314, 315, 320 enters the nanoslit 223 from the lateral input aperture of the biosensor 221 to the lateral output aperture 222, with a flow front 301. Molecules 311, 312, 313, 314, 315, 320 may interact with the different immobilized biomarkers 331, 332, 333, 334, 335, 336 and may form complexes 341, 343, 344, 345, 346 if specific to the biomarkers. The laser beam 510 monitors the concentration of the immobilized biomolecules on their specific biomarkers in the detection volume 520. Molecules 320 that are not specific to any functionalized biomarkers won't be measured by the system. Finally, negative control areas 335 and positive control areas 336 may for example be used to calibrate the biosensor.

FIG. 3 illustrates the principle of detection and the cross-section of a nanoslit 223 of a nanofluidic biosensor according to an embodiment of the invention. The biosensor comprises a nanoslit 223 extending from a lateral input aperture 221 to a lateral output aperture 222, thereby creating a fluidic connection between said apertures. A fluidic solution 300 containing fluorescently labeled specific biomolecules (311, 312, 313, 314, 315) and non-specific biomolecules 320 is filled into the biosensor, entering the biosensor from the input lateral aperture 221, flowing through the nanoslit 223 and to the output lateral aperture 222 with a flow front 301. In embodiments, various biomarkers (331, 332, 333, 334, 335, 336) are immobilized on various selectively functionalized structured surfaces 240. Remaining surfaces 250 of the nanofluidic biosensor are for example treated to avoid unwanted functionalization of biomarkers or non-specific binding of biomolecules. During the filling of the output lateral aperture and thanks to Brownian motion, biomolecules (311, 312, 313, 314, 315, 320) interact with the biomarkers (331, 332, 333, 334, 335, 336) immobilized inside the nanoslit 223 and may create molecular complexes (341, 342, 343, 344, 346). The non-specific biomolecules 320 will also diffuse in the nanoslit 223 but will not form molecular complexes with the immobilized biomarkers (331, 332, 333, 334, 335, 336).

In order to optimize the detection of a particular biomolecule, a detection volume 520 is focused inside the nanoslit 223 such that the intersection volume defined by the volume of the nanoslit 223 and the detection volume 520 is maximal, and located in one of the functionalized areas 240. When excited by a laser beam, the immobilized fluorescently emitting complexes 341, 342, 343, 344, 346, respectively, and the diffusing fluorescently emitting biomolecules 320 diffusing across the optical detection volume 520 are both detected by the optical system.

The present invention thus allows detecting and/or measuring different biomarkers or different concentrations of the same biomarker in a single nanofluidic biosensor. This allows benefiting from the potential of multiplexing detections or of performing calibration.

Figure 4A:
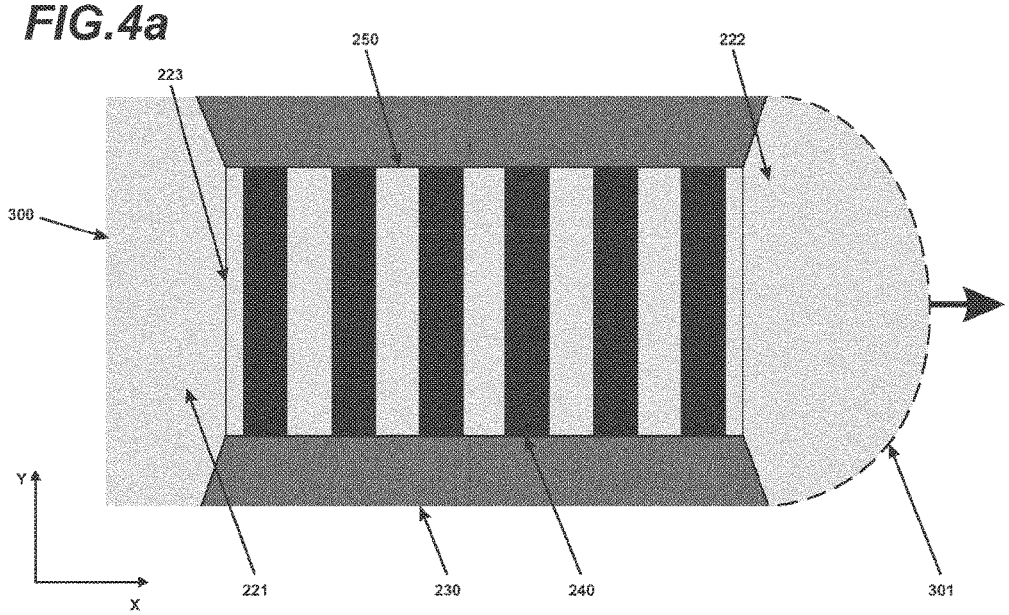

FIGS. 4a to 4c show a top-view cross section of a nanofluidic biosensor according to embodiments of the invention. A nanoslit 223 with a height defined by the thickness of a layer 230 is linked to an input lateral aperture 221 and to an output lateral aperture 222. A solution 300 containing biomolecules is filling the biosensor with a flow front 301. The nanoslit 223 comprises functionalized areas 240, 241, 242 and non-functionalized areas 250. As depicted in FIG. 4a, the functionalized areas may be lines or rectangles 240, small polygon structures 241 as illustrated in FIG. 4b or round or oval structures 242 as proposed in FIG. 4c. Any other shape is however possible within the scope of the invention.

Figure 5:
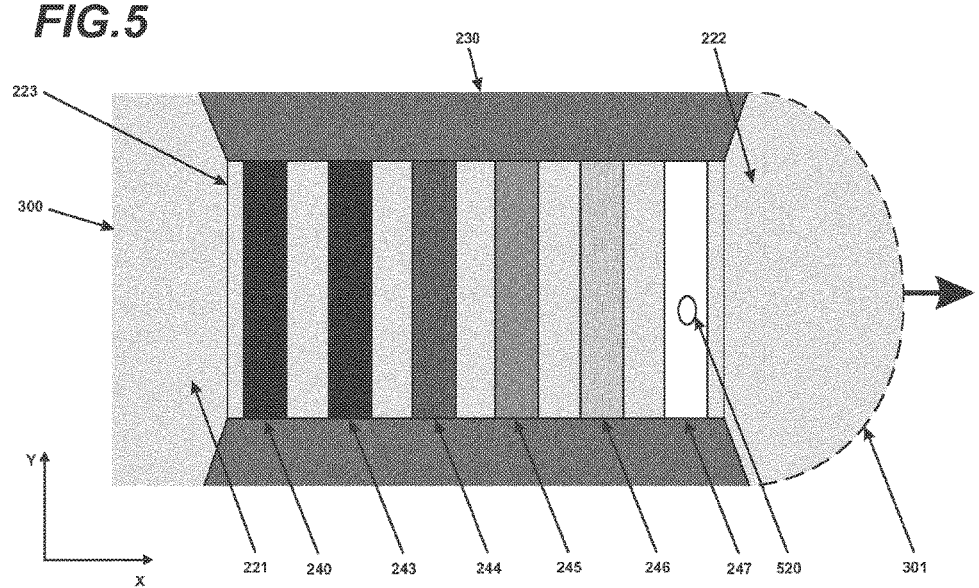
FIG. 5 is a partial top view cross sections of a biosensor according to still another embodiment of the invention, with a first functionalized area 240 for immobilizing one type of biomarker (specific detection), and other areas that are functionalized for the calibration of the test. For example, functionalized area 243 is the 100% positive control, functionalized area 244 is 75% positive control, functionalized area 245 is 50% positive control, functionalized area 246 is 25% positive control and functionalized area 247 the negative control. The laser beam 510 monitors the concentration of the immobilized biomolecules on their specific biomarkers in the detection volume 520 for each different functionalized area.

FIG. 5 illustrates an example of another embodiment of the present invention. According to the illustrated example, a first functionalized area 240 is prepared with a first type of biomarker, and the other functionalized areas 243, 244, 245, 246, 247 with another type of biomarker and are used to calibrate the result obtained with the first functionalized area 240. For example, a functionalized area 243 is 100% covered with a positive control biomarker and a functionalized area 247 is 100% covered with a negative control biomarker. Functionalized areas 244, 245 and 246 are only partially covered with a positive control biomarker. The partial coverage is for example performed by applying different patterns during the microfabrication of the functionalized areas 244, 245, 246 or by varying the concentration of the biomarker during the immobilization process. The laser spot 520 measuring the concentration of biomolecules is illustrated in the negative control functionalized area 247 in FIG. 5.

Figure 6:
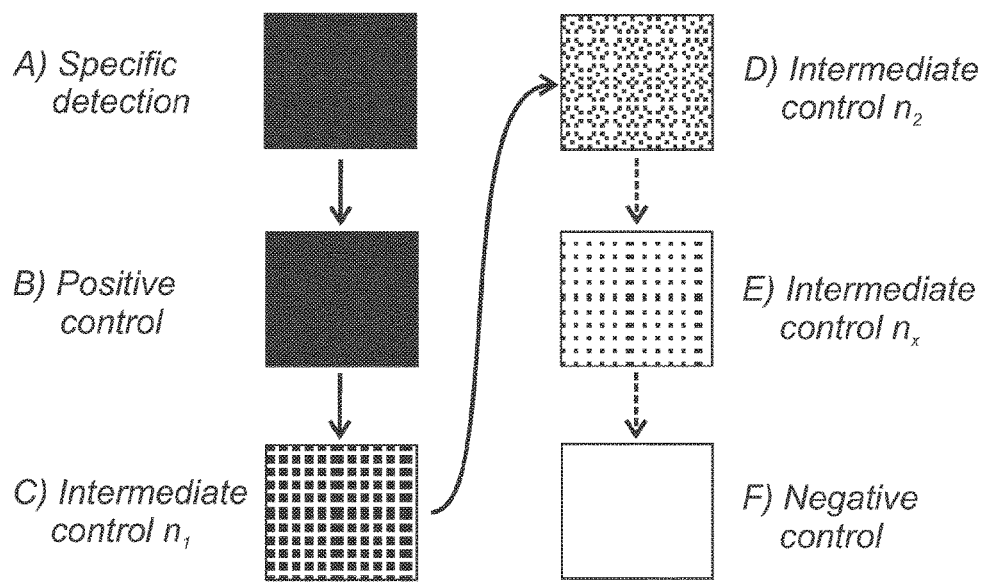
FIG. 6 illustrates the various sequences for the detection using a biosensor of FIG. 5. First the specific detection is measured in the functionalized area A), then the positive control B), several intermediate controls C), D), E), and finally the negative control F).

FIG. 6 schematically illustrates the method of calibrating a nanofluidic biosensor according to embodiments of the invention. Firstly, the laser beam measures the specific detection in the first functionalized area (A). Then, it measures a positive control (B), several intermediate control n1 (C), n2 (D), nx (E) and finally a negative control (F). Microfabricated patterns of the functionalized areas (in black) are also represented for each step.

Figure 7:
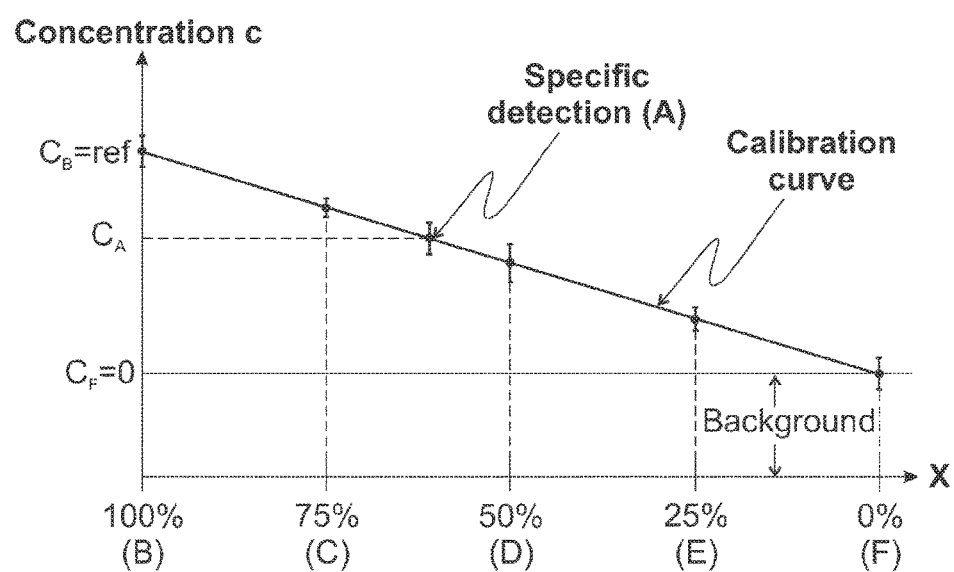
FIG. 7 represents a typical calibration curve, established from functionalized areas 243, 244, 245, 246 and 247, allowing calibrating the specific detection value (CA) in function of the biosensor environment (background, maximum value, etc.) and of the characteristics of the solution 300 (viscosity, density of biomolecules, etc.).

In order to calibrate the nanofluidic biosensor and thus to obtain an accurate quantitative specific detection, a calibration curve is measured for different concentration of control biomarkers. FIG. 7 illustrates a calibration curve. From measurements realized in the functionalized areas 243, 244, 245, 246 and 247, the specific detection value (CA) is for example adjusted in function of the biosensor environment (background, maximum value, etc.) and of the characteristics of the solution 300, such as for example the solution's viscosity, the density of biomolecules, etc.

According to the present invention, the definition of precise functionalization areas in a nanoslit provides for great improvements to the multiplexed detection and calibration of biomolecules interacting or not with other immobilized biomolecules. Applications of the present invention for example include biomedical, biological or food analysis as well as fundamental studies in analytical and bioanalytical chemistry.

The invention claimed is:

1. A biosensor for detecting and quantifying fluorescently-labeled biomolecules, said biosensor comprising:
   a lower substrate;
   an upper substrate stacked on said lower substrate;
   a nanoslit which is a microfabricated structure with one-nanometer-sized dimension, formed between said lower substrate and said upper substrate, said nanoslit comprising a plurality of local structured areas disposed along said nanoslit;
   a lateral input aperture in direct contact with said nanoslit, for letting a solution containing biomolecules enter said nanoslit; and
   a lateral output aperture in direct contact with said nanoslit, for driving said solution through said nanoslit, wherein the plurality of local structured areas are each functionalized by different biomarkers.

2. Biosensor according to claim 1 wherein said biologically or chemically interact with specific biomolecules contained in said solution.

3. Biosensor according to claim 1, wherein said plurality of biomarkers do not interact biologically or chemically with non-specific biomolecules contained in said solution.

4. Biosensor according to claim 1, wherein said lower and upper substrates are made of a material selected from the group comprising silicon, glass, plastic and oxide compounds.

5. Biosensor according to claim 1, wherein said lateral input aperture and said lateral output aperture each have an area from 100 $nm^2$ to 20 $mm^2$ and said nanoslit has at least one dimension between 2 nm and 1000 nm.

6. Biosensor according to claim 1 wherein the plurality of functionalized areas differ from each other in that they are functionalized by different types of biomarkers.

7. Biosensor according to claim 1 wherein the plurality of functionalized areas differ from each other in that they are functionalized by different densities of biomarkers.

8. An array comprising a plurality of biosensors according to claim 1, said biosensors being in a fixed position relative to each other inside a system.

9. Assembly comprising at least one biosensor according to claim 1, and further comprising optical means for fluorescence excitation and detection.

10. Assembly according to claim 9, wherein said optical means is a fluorescence measurement unit comprising a single-photon detector.

11. Assembly according to claim 9, wherein said single-photon detector is a CMOS or CCD detector array.

12. Assembly according to claim 9, wherein said single-photon detector is an avalanche photodiode (APD).

13. Assembly according to claim 9, wherein said single-photon detector is a photomultiplier tube (PMT).

14. A method for detecting and quantifying the presence of fluorescently-labeled biomolecules in a solution, said method comprising the steps of:
   a) providing at least one biosensor according to claim 1;
   b) filling said at least one biosensor with an aqueous solution, from a lateral input aperture of said at least one biosensor, across a nanoslit of said at least one biosensor, towards a lateral output aperture of said at least one biosensor, by depositing said aqueous solution into said lateral input aperture, wherein said aqueous solution contains fluorescently-labeled biomolecules that can be specific to a plurality of biomarkers immobilized on a plurality of local structured areas of said nanoslit;

c) detecting specific complexes made of fluorescently-labelled biomolecules immobilized on said plurality of biomarkers inside said nanoslit by measuring with an optical system the fluorescence intensity of fluorophores attached to said specific complexes, wherein said plurality of local structured areas are patterned for immobilizing different biomarkers, and d) quantifying the presence of fluorescently-labelled biomolecules in the solution based on the fluorescence intensity measured with the optical system.

15. Method according to claim 14, wherein said fluorescently-labeled biomolecules are proteins, DNA, RNA, antibodies, amino acids, nucleic acids, enzymes, lipid molecules, peptides, polysaccharides and/or viruses.

* * * * *